US010463312B2

(12) United States Patent
Bhattacharya et al.

(10) Patent No.: US 10,463,312 B2
(45) Date of Patent: Nov. 5, 2019

(54) METHODS AND SYSTEMS FOR PREDICTING MORTALITY OF A PATIENT

(71) Applicant: Conduent Business Services, LLC, Dallas, TX (US)

(72) Inventors: Sakyajit Bhattacharya, Bangalore (IN); Vaibhav Rajan, Bangalore (IN); Harsh Shrivastava, Bangalore (IN)

(73) Assignee: CONDUENT BUSINESS SERVICES, LLC, Florham Park, NJ (US)

( * ) Notice: Subject to any disclaimer, the term of this patent is extended or adjusted under 35 U.S.C. 154(b) by 1100 days.

(21) Appl. No.: 14/841,812

(22) Filed: Sep. 1, 2015

(65) Prior Publication Data

US 2017/0055916 A1 Mar. 2, 2017

(51) Int. Cl.
| | |
|---|---|
| *A61B 5/00* | (2006.01) |
| *G16H 50/30* | (2018.01) |
| *G16H 50/20* | (2018.01) |
| *A61B 5/0205* | (2006.01) |
| *A61B 5/145* | (2006.01) |
| *A61B 5/021* | (2006.01) |
| *A61B 5/024* | (2006.01) |
| *A61B 5/08* | (2006.01) |
| *G16H 10/60* | (2018.01) |

(52) U.S. Cl.
CPC ......... *A61B 5/7275* (2013.01); *G16H 50/20* (2018.01); *G16H 50/30* (2018.01); *A61B 5/021* (2013.01); *A61B 5/024* (2013.01); *A61B 5/02055* (2013.01); *A61B 5/0816* (2013.01); *A61B 5/14542* (2013.01); *G16H 10/60* (2018.01)

(58) Field of Classification Search
CPC ......... G61H 10/60; G16H 50/20; G06F 19/00
See application file for complete search history.

(56) References Cited

U.S. PATENT DOCUMENTS

| | | |
|---|---|---|
| 7,877,228 B2 | 1/2011 | Ali |
| 2011/0106735 A1 | 5/2011 | Boult et al. |

(Continued)

OTHER PUBLICATIONS

Liu Ya-Qin, "Decision tree based predictive models for breast cancer survivability on imbalanced data", Aug. 2009, IEEE, pp. 1-3 (Year: 2009).*

(Continued)

*Primary Examiner* — Joy Chng
*Assistant Examiner* — Evangeline Barr
(74) *Attorney, Agent, or Firm* — Jones Robb, PLLC (57) ABSTRACT

Disclosed are embodiments of methods and systems for predicting mortality of a first patient. The method comprises categorizing a historical data into a first category and a second category. The method further comprises determining a first test parameter and a second test parameter based on at least one of a sample data of a first patient and the historical data corresponding to at least one of the first category and the second category. The method further comprises determining a probability score based on a cumulative distribution of at least one of the first test parameter and the second test parameter. The method further comprises categorizing the sample data in one of the first category and the second category based on the probability score. Further, the method comprises predicting the mortality of the first patient based on at least the categorization of the sample data of the first patient.

20 Claims, 4 Drawing Sheets

(56) References Cited

U.S. PATENT DOCUMENTS

| | | | |
|---|---|---|---|
| 2013/0197924 A1* | 8/2013 | Kocis | G06Q 50/22 |
| | | | 705/2 |
| 2013/0325498 A1 | 12/2013 | Muza, Jr. et al. | |
| 2014/0257122 A1 | 9/2014 | Ong et al. | |
| 2014/0379717 A1* | 12/2014 | Urmanov | G06K 9/6215 |
| | | | 707/738 |
| 2015/0213227 A1* | 7/2015 | Vairavan | G06N 7/005 |
| | | | 706/12 |

OTHER PUBLICATIONS

Diethelm Wuertz, many others, and see the Source file. fAsianOptions: EBM and Asian Option Valuation, 2009. R package version, 2100.76.

Nitesh V Chawla. Data mining for imbalanced datasets: An overview. In Data mining and knowledge discovery handbook, pp. 853-867. Springer, 2005.

Milton Abramowitz and Irene A Stegun. Handbook of Mathematical Functions: with Formulas, Graphs, and Mathematical Tables. Dover Publications, 1972.

Alistair E.W. Johnson, Nic Dunkley, Louis Mayaud, Athanasios Tsanas, Andrew A. Kramer, and Gary D. Clifford. Patient specific predictions in the intensive care unit using a bayesian ensemble. In Computers in Cardiology, 2012. IEEE, 2012.

Ikaro Silva, George Moody, Daniel J. Scott, Leo A. Celi, and Roger G. Mark. Predicting in-hospital mortality of icu patients: The physionet/computing in cardiology challenge 2012. In Computers in Cardiology, 2012. IEEE, 2012.

* cited by examiner

METHODS AND SYSTEMS FOR PREDICTING MORTALITY OF A PATIENT

TECHNICAL FIELD

The presently disclosed embodiments are related, in general, to healthcare systems. More particularly, the presently disclosed embodiments are related to a method and a system for predicting mortality of a patient.

BACKGROUND

Healthcare industry may be an aggregation of one or more sectors that individually or in combination may provide one or more services to patients. The one or more sectors may include, but are not limited to, a pharmaceutical sector and a diagnostic sector. Advancements and automations in patient record management systems have led to development of systems that may have a capability of storing and managing patient records in an electronic format. Typically, the patient records may include various medical records of the patients such as, but are not limited to, lab investigation records, vital sign records, and mortality records. Further, such patient record management systems may utilize one or more models to categorize the patient records in one or more categories.

In certain scenarios, a number of medical records in a category from the one or more categories may be less in comparison to the number of medical records in other categories from the one or more categories. For example, 4000 medical records of patients were obtained. Out of 4000 patients, it was found that 534 patients had died (minority category) while remaining patients had survived (majority category). In such a case, the one or more models so learnt on such imbalanced dataset may tend to make classification errors.

SUMMARY

According to embodiments illustrated herein there is provided a method for predicting mortality of a first patient. The method comprises extracting, by one or more processors, historical data associated with one or more second patients, wherein the historical data comprises a measure of one or more physiological parameters associated with each of the one or more second patients. Thereafter, the historical data of the one or more second patients is categorized into a first category and a second category based on at least a mortality status associated with each of the one or more second patients, wherein a number of records in the first category and the second category is imbalanced. Further, the method comprises receiving, by the one or more processors, a sample data of the first patient comprising at least the measure of the one or more physiological parameters associated with the first patient. The method further comprises determining, by the one or more processors, a first test parameter and a second test parameter based on at least one of the sample data of the first patient and the historical data of the one or more second patients corresponding to at least one of the first category and the second category. The method further comprises determining, by the one or more processors, a probability score based on a cumulative distribution of at least one of the first test parameter and the second test parameter. Thereafter, the method comprises categorizing, by the one or more processors, the sample data of the first patient, in one of the first category and the second category, based on a comparison between the probability score and a predetermined threshold value. Further, the method comprises predicting, by the one or more processors, the mortality of the first patient based on at least the categorization of the sample data of the first patient.

According to embodiment illustrated herein there is provided a system for predicting mortality of a first patient. The system comprises one or more processors configured to extract historical data associated with one or more second patients. The historical data comprises a measure of one or more physiological parameters associated with each of the one or more second patients. Thereafter, the one or more processors are configured to categorize the historical data of the one or more second patients into a first category and a second category based on at least a mortality status associated with each of the one or more second patients, wherein a number of records in the first category and the second category is imbalanced. The one or more processors are further configured to receive a sample data of the first patient comprising at least the measure of the one or more physiological parameters associated with the first patient. The one or more processors are further configured to determine a first test parameter and a second test parameter based on at least one of the sample data of the first patient and the historical data of the one or more second patients corresponding to at least one of the first category and the second category. The one or more processors are further configured to determine a probability score based on a cumulative distribution of at least one of the first test parameter and the second test parameter. The one or more processors are further configured to categorize the sample data of the first patient, in one of the first category and the second category, based on a comparison between the probability score and a predetermined threshold value. The one or more processors are further configured to predict the mortality of the first patient based on at least the categorization of the sample data of the first patient.

According to embodiment illustrated herein there is provided a computer program product for use with a computing device. The computer program product comprising a non-transitory computer readable medium. The non-transitory computer readable medium stores a computer program code for predicting mortality of a first patient. The computer program code is executable by one or more processors in the computing device to extract historical data associated with one or more second patients. The historical data comprises a measure of one or more physiological parameters associated with each of the one or more second patients. The computer program code is further executable by the one or more processors in the computing device to categorize the historical data of the one or more second patients into a first category and a second category based on at least a mortality status associated with each of the one or more second patients, wherein a number of records in the first category and the second category is imbalanced. The computer program code is further executable by the one or more processors in the computing device to receive a sample data of the first patient comprising at least the measure of the one or more physiological parameters associated with the first patient. The computer program code is further executable by the one or more processors in the computing device to determine a first test parameter and a second test parameter based on at least one of the sample data of the first patient and the historical data of the one or more second patients corresponding to at least one of the first category and the second category. The computer program code is further executable by the one or more processors in the computing device to determine a probability score based on a cumulative distribution of at least one of the first test parameter and the second test parameter. The computer program code is further executable by the one or more processors in the computing device to categorize the sample data of the first patient, in one of the first category and the second category, based on a comparison between the probability score and a predetermined threshold value. The computer program code is further executable by the one or more processors in the computing device to predict the mortality of the first patient based on at least the categorization of the sample data of the first patient.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not limit, the scope in any manner, wherein similar designations denote similar elements, and in which.

DETAILED DESCRIPTION

The present disclosure is best understood with reference to the detailed figures and descriptions set forth herein. Various embodiments are discussed below with reference to the figures. However, those skilled in the art will readily appreciate that the detailed descriptions given herein with respect to the figures are simply for explanatory purposes, as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "at least one embodiment," "an embodiment," "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

Definitions: The following terms shall have, for the purposes of this application, the respective meanings set forth below.

A "computing device" refers to a device that includes one or more processors/microcontrollers and/or any other electronic components, a device, or a system that performs one or more operations according to one or more programming instructions/codes stored in one or more memories. Examples of the computing device may include, but are not limited to, a desktop computer, a laptop, a PDA, a mobile device, a smartphone, a tablet computer (e.g., iPad® and Samsung GalaxyTab®), and the like.

A "mortality status" refers to a living state or a condition of an individual who is under medical observations. For example, the mortality status of an individual may be either "alive" or "died".

A "patient" refers to an individual or a living entity who may be suffering from a disease or a health condition. In an embodiment, the patient may seek a medical opinion, pertaining to the disease or the health condition, by a medical expert such as a doctor. In another words, the patient is a recipient of one or more health care services.

A "first patient" refers to a patient who is currently under medical observations. In another embodiment, the first patient is the patient whose health condition (e.g., mortality) is to be predicted.

A "second patient" refers to a patient who was under medical observations in the past. The second patient may have died or survived based on his/her health conditions and/or undergone treatments while he/she was under the medical observations.

A "multivariate dataset" refers to a dataset that includes observations of a p-dimensional variable. For example, "n" observations of p-dimensional variable may constitute a multivariate dataset. For example, a medical record data may include a measure of one or more physiological parameters of one or more patients, where the one or more physiological parameters correspond to the p-dimensions and the one or more patients correspond to the n observations. Such medical record data is an example of the multivariate dataset.

"Vital signs" refer to a measure of one or more physiological parameters that may be indicative of an individual's health condition. The vital signs may point to a potential disease or a recovery from a health condition. In an embodiment, the vital signs may comprise at least a measure of one or more of, but are not limited to, a blood pressure, a heart rate, a respiratory rate, a body temperature, and an oxygen saturation level. Hereinafter, "vital signs" and "physiological parameters" may be interchangeably used.

"Historical data" refer to one or more medical records of one or more second patients who were under medical observations in the past. In an embodiment, the one or more medical records may comprise a measure of one or more physiological parameters (e.g., blood pressure, heart rate, respiratory rate, body temperature, etc.) associated with the one or more second patients. Further, the one or more medical records may comprise lab investigation data (e.g., a sodium level, a potassium level, a glucose level, etc.), diagnostics data, and other medical data associated with the one or more second patients. In an embodiment, the historical data may further comprise a health condition (e.g., a mortality status) of each of the one or more second patients at the time of discharge. In an embodiment, the historical data may correspond to a multivariate dataset.

A "sample data" refers to a medical record of a patient who is presently under medical observations. The sample data may comprise at least a measure of one or more physiological parameters, one or more lab investigation data, or diagnostic data associated with the patient under the medical observations. In an embodiment, the sample data may be represented by a multivariate dataset.

"Probability" shall be broadly construed, to include any calculation of probability; approximation of probability, using any type of input data, regardless of precision or lack of precision; any number, either calculated or predetermined, that simulates a probability; or any method step having an effect of using or finding some data having some relation to a probability.

A "probability distribution" refers to an assignment of probability to each measureable subset of possible outcomes of a random experiment.

A "cumulative distribution" refers to a distribution function that describes a probability that a real-valued random variable X with a given probability distribution will be found at a value less than or equal to x.

A "Gaussian distribution" refers to a function that describes a probability that any real observation may fall between any two real limits or real numbers, as a curve may approach zero on either side.

"Hypothesis testing" refers to a method of statistical inference that utilizes statistics to determine a probability that a given hypothesis is true. The process of hypothesis testing comprises at least four steps. In a first step, a null hypothesis $H_0$ and an alternate hypothesis $H_1$ may be formulated. In a second step, one or more test parameters are determined that may be used to assess validity of the null hypothesis. In a third step, a probability score is determined assuming that the null hypothesis is true. In a fourth step, the determined probability score is compared with a predetermined threshold value a. In an embodiment, the null hypothesis may be ruled out, when the probability score is less than the predetermined threshold value a. In such a case, the alternate hypothesis may be validated based on the above mentioned steps.

A "classifier" refers to a mathematical model that may be configured to categorize a sample data into one or more categories. In an embodiment, the classifier is trained based on a historical data associated with one or more second patients who might be under medical observations in the past. Examples of the classifier may include, but are not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier.

"Training" refers to a process of updating/tuning a classifier using at least a historical data such that the classifier may be able to predict at least a category, from one or more categories, in which a sample data may be categorized.

An "imbalanced data" refers to an imbalance in a count of records in one or more categories. For instance, if a count of records in one category is much more than the count of records in the remaining one or more categories, then such records may correspond to the imbalanced data. For example, there are 4000 patients. Among these patients, 333 patients had died while they were under medical observations and the remaining patients (i.e., 3667) had survived. Such a dataset may correspond to the imbalanced data.

A "test parameter" refers to a set of values, which may be determined based on one or more physiological parameters and/or one or more lab investigation data associated with a first patient and one or more second patients. In an embodiment, the test parameter may be determined based on statistical analysis of the one or more physiological parameters and/or the one or more lab investigation data. In an embodiment, the statistical analysis may include one or more of, but are not limited to, mean, variance, co-variance, and standard deviation.

Figure 1:
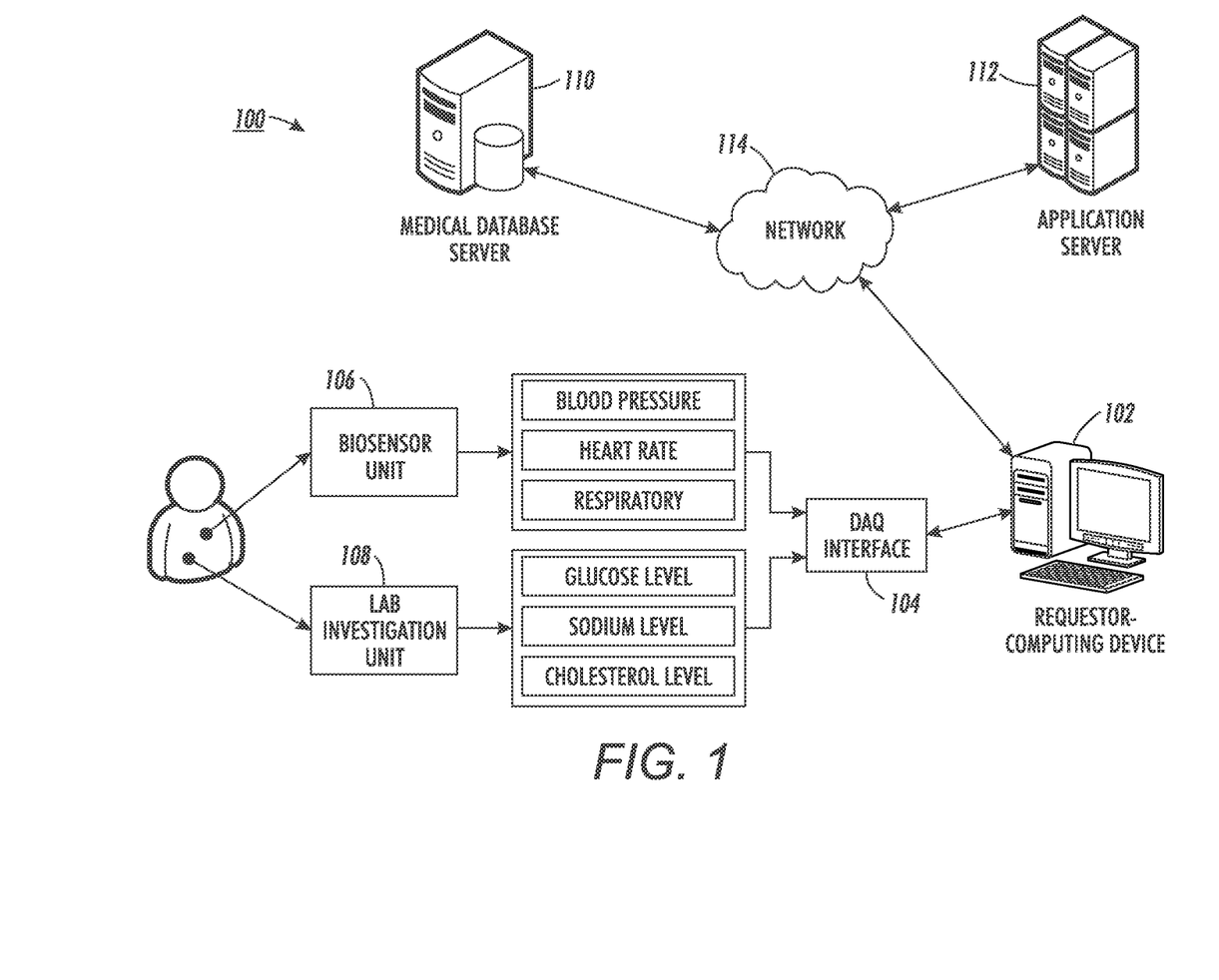
FIG. 1 is a block diagram of a system environment, in which various embodiments can be implemented.

FIG. 1 is a block diagram illustrating a system environment 100 in which various embodiments may be implemented. The system environment 100 includes a requestor-computing device 102, a data acquisition (DAQ) interface 104, a biosensor unit 106, a lab investigation unit 108, a medical database server 110, an application server 112, and a network 114. Various devices in the system environment 100 may be interconnected over the network 114. FIG. 1 shows, for simplicity, one requestor-computing device 102, one DAQ interface 104, one biosensor unit 106, one lab investigation unit 108, one medical database server 110, and one application server 112. However, it will be apparent to a person having ordinary skill in the art that the disclosed embodiments may also be implemented using multiple user-computing devices, multiple DAQ interfaces, multiple biosensor units, multiple lab investigation units, multiple medical database servers, and multiple applications servers.

The requestor-computing device 102 refers to a computing device used by a requestor (e.g., one or more healthcare professionals such as a doctor or one or more service providers such as a third party). The requestor-computing device 102 may include one or more processors and one or more memories. The one or more memories may include computer readable code that may be executable by the one or more processors to perform one or more operations. In an embodiment, the requestor-computing device 102 may be coupled to the DAQ interface 104. In an embodiment, the requestor-computing device 102 may be configured to receive a measure one or more physiological parameters of a first patient through the DAQ interface 104. Example of the one or more physiological parameters may include the measure of one or more of, but are not limited to, a blood pressure, a heart rate, a respiratory rate, a body temperature, and an oxygen saturation level. Further, the requestor-computing device 102 may be configured to receive one or more lab investigation data of the first patient from a lab investigation unit 116 through the DAQ interface 104. Example of the one or more lab investigation data may include the measure of one or more of, but are not limited to, a sodium level, a potassium level, and a glucose level. In another embodiment, the requestor-computing device 102 may be configured to receive the one or more physiological parameters and the one or more lab investigation data of the first patient over the network 114.

In an embodiment, the requestor may utilize the requestor-computing device 102 to transmit the one or more physiological parameters and the one or more lab investigation data associated with the first patient to the medical database server 110 or the application server 112. Hereinafter, the measure of the one or more physiological parameters and the measure of the one or more lab investigation data associated with the first patient have been referred to as a sample data. In an embodiment, the requestor may utilize the requestor-computing device 102 to provide an input pertaining to a prediction of mortality of the first patient.

The requestor-computing device 102 may include a variety of computing devices such as, but not limited to, a laptop, a PDA, a tablet computer, a smartphone, a phablet, and the like.

The DAQ interface 104 may comprise suitable logic, circuitry, interfaces, and/or code that may be operable to convert one or more measured parameters (e.g., the one or more physiological parameters or the one or more lab investigation data) into one or more digital numeric values that may be processed by a computing device. In an embodiment, the DAQ interface 104 may be coupled to the biosensor unit 106 and the lab investigation unit 108. In an embodiment, the DAQ interface 104 may include one or more communication interfaces such as a Universal Serial Bus (USB) Port, a FireWire Port, an IEEE 1394 standard based connector, and any other serial/parallel data interfacing connector known in the art to connect to the biosensor unit 106 and the lab investigation unit 108. In an embodiment, the DAQ interface 104 may perform one or more operations on the one or more measured parameters obtained from the biosensor unit 106 and the lab investigation unit 108. In an embodiment, the one or more operations may comprise, but are not limited to, conversion of one or more measured parameters to one or more signals, conversion of the one or more signals to one or more conditioned signals, and conversion of the one or more conditioned signals to one or more digitals values. In an embodiment, the DAQ interface 104 may be realized using one or more sensors, one or more signal conditioning circuits, one or more analog-to-digital converters, and one or more digital-to-analog converters.

A person having ordinary skill in the art will appreciate that the scope of the disclosure is not limited to the DAQ interface 104 to be implemented as independent from the requestor-computing device 102. In an embodiment, the DAQ interface 104 may be implemented within the requestor-computing device 102 without departing from the scope of the disclosure.

The biosensor unit 106 may comprise suitable logic, circuitry, interfaces, and/or code that may be operable to measure the one or more physiological parameters. The biosensor unit 106 may include one or more biosensors that may be connected to the first patient. Each of the one or more biosensors may be configured to measure the one or more physiological parameters of the first patient. In an embodiment, the biosensor unit 106 may be coupled to the DAQ interface 104. In another embodiment, the biosensor unit 106 may be connected to the requestor-computing device 102 through a wireless connection such as, but not limited to, a Bluetooth based connection, a Near Field Communication (NFC) based connection, a Radio Frequency Identification (RFID) based connection, or any other wireless communication protocol. Various types of the one or more biosensors may include, but are not limited to, a blood glucose biosensor, a piezoelectric biosensor, an acoustic wave biosensors, amperometric biosensor, and the like.

A person having ordinary skill in the art will understand that the scope of the disclosure should not be limited to the measurement of the one or more physiologically parameters using the aforementioned biosensor unit 106 and using the aforementioned one or more biosensors. Further, the examples provided in supra are for illustrative purposes and should not be construed to limit the scope of the disclosure.

The lab investigation unit 108 may comprise suitable logic, circuitry, interfaces, and/or code that may be operable to measure the one or more lab investigation data of the first patient In an embodiment, the lab investigation unit 108 may comprise one or more instruments that may be configured to measure the one or more lab investigation data such as, but are not limited to, a sodium level, a potassium level, a glucose level, and a cholesterol level associated with the first patient. In an embodiment, the lab investigation unit 108 may be coupled to the DAQ interface 104. In another embodiment, the lab investigation unit 108 may be connected to the requestor-computing device 102 through a wireless connection such as, but not limited to, a Bluetooth based connection, a Near Field Communication (NFC) based connection, a Radio Frequency Identification (RFID) based connection, or any other wireless communication protocol. The lab investigation unit 108 may utilize one or more of, but are not limited to, a microscope, an electrophoresis apparatus, an oscilloscope, an electrolyte analyser, and the like to measure the one or more lab investigation data.

A person having ordinary skill in the art will understand that the scope of the disclosure should not be limited to the measurement of the one or more lab investigation data using the aforementioned lab investigation unit 108. Further, the examples provided in supra are for illustrative purposes and should not be construed to limit the scope of the disclosure.

The medical database server 110 may refer to a computing device, which may be configured to store a historical data of the one or more second patients who were under medical observations in past. The historical data may comprise the measure of the one or more physiological parameters and the one or more lab investigation data of each of the one or more second patients while the one or more second patients were under the medical observations. The historical data may further include the mortality status (e.g., alive or dead) of each of the one or more second patients. In an embodiment, the medical database server 110 may extract the information pertaining to the one or more physiological parameters and the one or more lab investigation data from one or more medical records associated with each of the one or more second patients. In an embodiment, the medical database server 110 may receive the one or more medical records from the requestor-computing device 102. For example, an individual associated with a healthcare organization may be responsible to update the medical database server 110. In another embodiment, the medical database server 110 may receive the one or more medical records from one or more external repositories. For example, a medical repository maintained by a third party.

In addition, in an embodiment, the medical database server 110 may be configured to store the sample data of the first patient. The medical database server 110 may receive the sample data from the requestor-computing device 102.

In an embodiment, the medical database server 110 may receive one or more queries from the application server 112 to extract the historical data pertaining to the one or more second patients and/or the sample data pertaining to the first patient. The medical database server 110 may be realized through various technologies such as, but not limited to, Oracle®, IBM DB2®, Microsoft SQL Server®, Microsoft Access®, PostgreSQL®, MySQL® and SQLite®, and the like. In an embodiment, the application server 112 may connect to the medical database server 110 using one or more protocols such as, but not limited to, Open Database Connectivity (ODBC) protocol and Java Database Connectivity (JDBC) protocol.

The application server 112 refers to a computing device that may include one or more processors and one or more memories. The one or more memories may include computer readable code that may be executable by the one or more processors to perform one or more operations. For example, the one or more operations may include one or more of, but are not limited to, categorizing a historical data into a first category and a second category, training a classifier to categorize a sample data of a first patient into the first category or the second category, and predicting a mortality of the first patient based on at least the categorization. In an embodiment, the application server 112 may connect to the medical database server 110, to extract the historical data, using one or more protocols such as, but not limited to, Open Database Connectivity (ODBC) protocol and Java Database Connectivity (JDBC) protocol.

The application server 112 may be realized through various types of application servers such as, but not limited to, Java application server, .NET framework application server, and Base4 application server. A person having ordinary skill in the art will understand that the scope of the disclosure is not limited to the medical database server 110 or the application server 112 as a separate entity. In an embodiment, the functionalities of the medical database server 110 may be integrated into the application server 102 without departing from the spirit of the disclosure.

A person having ordinary skill in the art will understand that the scope of the disclosure is not limited to the requestor-computing device 102 or the application server 112 as separate entity. In an embodiment, the application server 102 may be realized as an application hosted on or running on the requestor-computing device 102 without departing from the spirit of the disclosure.

The network 114 corresponds to a medium through which content and messages flow between various devices of the system environment 100 (e.g., the requestor-computing device 102, the medical database server 110, and the application server 112). Examples of the network 114 may include, but are not limited to, a Wireless Fidelity (Wi-Fi) network, a Wireless Area Network (WAN), a Local Area Network (LAN), or a Metropolitan Area Network (MAN). Various devices in the system environment 100 can connect to the network 114 in accordance with various wired and wireless communication protocols such as Transmission Control Protocol and Internet Protocol (TCP/IP), User Datagram Protocol (UDP), and 2G, 3G, or 4G communication protocols.

Figure 2:
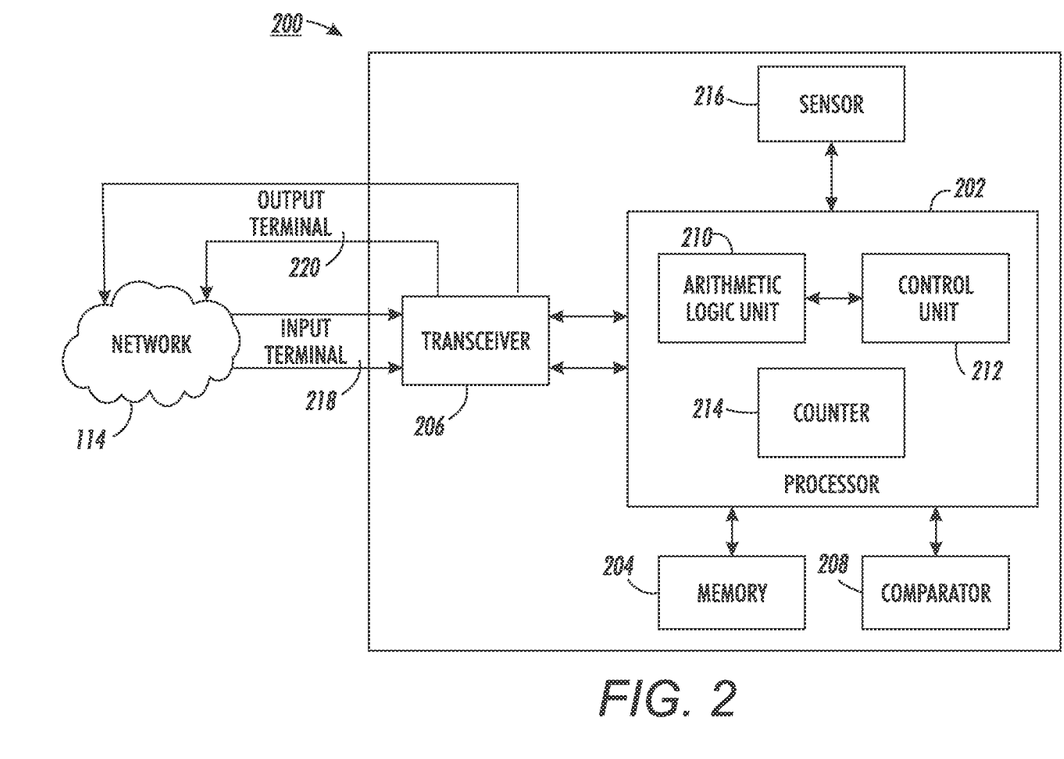
FIG. 2 is a block diagram of a system for predicting mortality of a first patient, in accordance with at least one embodiment.

FIG. 2 is a block diagram of a system 200 for predicting the mortality of the first patient, in accordance with at least one embodiment. In an embodiment, the system 200 may correspond to the requestor-computing device 102 or the application server 112. For the purpose of ongoing description, the system 200 is considered as the application server 112. However, the scope of the disclosure should not be limited to the system 200 as the application server 112. The system 200 may also be realized as the requestor-computing device 102, without departing from the spirit of the disclosure.

The system 200 may include one or more processors, such as a processor 202, one or more memories, such as a memory 204, one or more transceivers, such as a transceiver 206, one or more comparators, such as a comparator 208, and one or more sensors, such as a sensor 216. The transceiver 206 may be coupled with an input terminal 218 and an output terminal 220. The transceiver 206 may connected to the network 114 through the input terminal 218 and the output terminal 220.

The processor 202 may include suitable logic, circuitry, and interfaces and may further be configured to execute one or more instructions stored in the memory 204 to perform one or more operations. The processor 202 may be coupled to the memory 204, the transceiver 206, the comparator 208 and the sensor 216. The processor 202 may comprise one or more arithmetic logic units such as an arithmetic logic unit (ALU) 210 and one or more control units such as a control unit 212. The ALU 210 may be coupled to the control unit 212. The ALU 210 may be operable to perform one or more mathematical and logical operations. The control unit 212 may be configured to control the operation of the ALU 210. Though, the ALU 210 and the control unit 212 are implemented within the processor 202 in FIG. 2, a person skilled in the art will appreciate that the ALU 210 and the control unit 212 may be implemented independently from the processor 202 without departing from the scope of the disclosure. The processor 202 may further comprise one or more counters such as a counter 214. The processor 202 may be implemented based on a number of processor technologies known in the art. Examples of the processor 202 include, but are not limited to, an X86-based processor, a Reduced Instruction Set Computing (RISC) processor, an Application-Specific Integrated Circuit (ASIC) processor, and/or a Complex Instruction Set Computing (CISC) processor.

The memory 204 may be operable to store one or more machine codes, and/or computer programs having at least one code section executable by the processor 202. The memory 204 may further be configured to store the one or more medical records associated with the one or more second patients and/or the first patient. Some of the commonly known memory implementations include, but are not limited to, a random access memory (RAM), a read-only memory (ROM), a hard disk drive (HDD), and a secure digital (SD) card. In an embodiment, the memory 204 may include the one or more machine codes, and/or computer programs that are executable by the processor 202 to perform specific operations. It will be apparent to a person having ordinary skill in the art that the one or more instructions stored in the memory 204 may enable the hardware of the system 200 to perform the one or more operations.

The transceiver 206 may be operable to communicate with the one or more devices, such as the requestor-computing device 102, and/or one or more servers, such as the medical database server 110 over the network 114. The transceiver 206 may be operable to transmit or receive the instructions/queries/historical data/sample data or other information to/from various components of the system environment 100. In an embodiment, the transceiver 206 is coupled to the input terminal 218 and the output terminal 220 through which the transceiver 206 may receive or transmit instructions/queries/historical data/sample data or other information corresponding to the prediction of the mortality of the first patient. In an embodiment, the input terminal 218 and the output terminal 220 may be realized through, but are not limited to, an antenna, an Ethernet port, an USB port or any other port that can be configured to receive and transmit data. The transceiver 206 may receive and transmit various data in accordance with various communication protocols such as, TCP/IP, UDP, and 2G, 3G, or 4G communication protocols through the input terminal 218 and the output terminal 220, respectively.

The comparator 208 may be configured to compare at least two input signals to generate an output signal. In an embodiment, the output signal may correspond to either "1" or "0." In an embodiment, the comparator 208 may be configured to generate output "1" if the value of a first signal (from the at least two signals) is greater than the value of a second signal (from the at least two signals). Similarly, the comparator 208 may be configured to generate an output "0" if the value of the first signal is less than the value of the second signal. In an embodiment, the comparator 208 may be realized through either software technologies or hardware technologies known in the art. Though, the comparator 208 is depicted as independent from the processor 202 in FIG. 2, a person skilled in the art will appreciate that the comparator 208 may be implemented within the processor 202 without departing from the scope of the disclosure.

The sensor 216 may comprise suitable logic, circuitry, and/or interfaces that may be operable to store a machine code and/or a computer program with at least one code section executable by the processor 202 The sensor 216 may correspond to a device that detects events or changes in quantities and provides a corresponding output, generally as an electrical or optical signal. In an embodiment, the sensor 216 may correspond to a bio-sensor, which may be configured to measure the one or more physiological parameters of the first patient. In an embodiment, the sensor 216 may be inbuilt within the system 200. Alternatively, the sensor 216 may be a separate device, which may be communicatively or otherwise coupled to the system 200.

Figure 3:
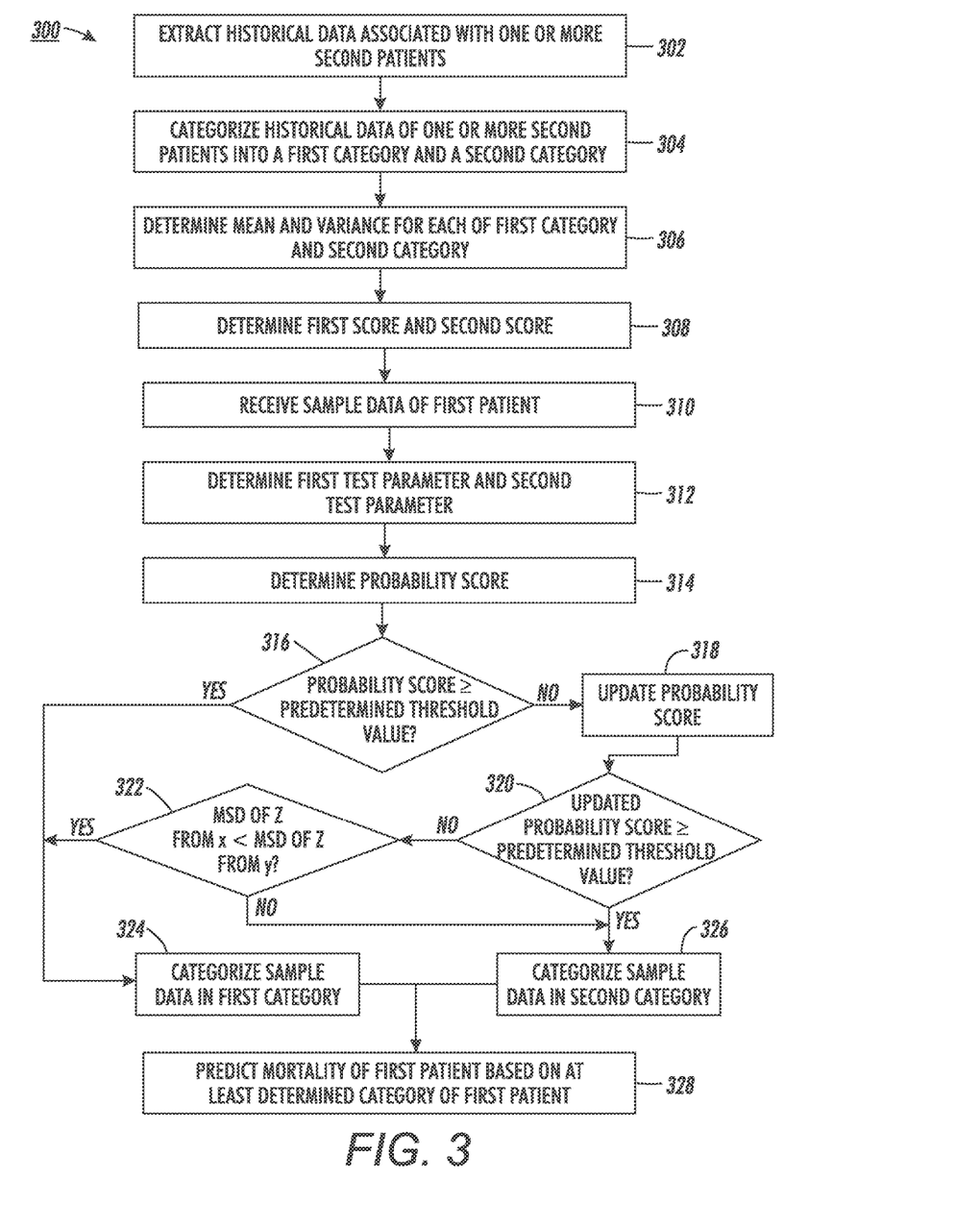
FIG. 3 is a flowchart illustrating a method for predicting mortality of a first patient, in accordance with at least one embodiment.

The operation of the system 200 has been described in conjunction with FIG. 3.

FIG. 3 illustrates a flowchart 300 of a method for predicting the mortality of the first patient, in accordance with at least one embodiment. The flowchart 300 has been described in conjunction with FIG. 1 and FIG. 2.

At step 302, the historical data associated with the one or more second patients is extracted. In an embodiment, the processor 202 may be configured to extract the historical data from the medical database server 110. In a scenario where the historical data is stored in the memory 204, the processor 202 may extract the historical data from the memory 204. In an embodiment, the historical data may include the one or more medical records of the one or more second patients. In an embodiment, the historical data may correspond to a multivariate healthcare dataset, which may include the measure of the one or more physiological parameters and/or the one or more lab investigation data of each of the one or more second patients. Examples of the one or more physiological parameters may include, but are not limited to, the measure of one or more of the blood pressure, the heart rate, the respiratory rate, the body temperature, and the oxygen saturation. Example of the one or more lab investigation data may include, but are not limited to, the measure of one or more of a sodium level, a potassium level, a glucose level, and a cholesterol level. In an embodiment, the historical data may further include the mortality status of each of the one or more second patients. In an embodiment, the mortality status of a second patient is indicative of whether the second patient had died or survived when the second patient was under the medical observations.

A person having ordinary skill in the art will understand that the scope of disclosure is not limited to the aforementioned one or more physiological parameters and the one or more lab investigation data. In an embodiment, various other physiological parameters and lab investigation data may be used without departing from the scope of the disclosure. Further, a person having ordinary skills in the art will appreciate that the historical data may include data of various data types such as, but not limited to, a numerical data type or a categorical data type. For example, in the historical data, the measure of the one or more physiological parameters may be numerical data type. Further, in the historical data, the gender of the second patient may be categorical data type.

At step 304, the historical data of the one or more second patients are categorized into the first category and the second category based on the mortality status associated with each of the one or more second patients. In an embodiment, the processor 202 may be configured to categorize the historical data of the one or more second patients in the first category and/or the second category based on the mortality status associated with each of the one or more second patients. In an embodiment, the mortality status of a second patient may correspond to a fact that may be representative of whether the second patient had survived while the second patient was under the medical observations. For example, a patient (namely, ABC) had died while he was under medical observations. In such a case, the processor 202 may categorize the historical data of the patient ABC into a second category. Another patient (namely, XYZ) had survived while he was under the medical observations. In such a case, the processor 202 may categorize the historical data of the patient XYZ into the first category.

Therefore, the first category may comprise the one or more medical records (or the historical data) of the one or more second patients who might have survived while they were under the medical observations. The second category may comprise the one or more medical records (or the historical data) of the one or more second patients, who might have died while they were under the medical observations.

A person having ordinary skills in the art will appreciate that a count of second patients who might have died will be much less in comparison to the count of second patients who might have survived. Therefore, the count of medical records corresponding the one or more second patients in the second category may be much less than the count of medical records corresponding to the one or more second patients in the first category. Thus, the second category may be a minority category and the first category may be a majority category.

At step 306, a mean and a variance of the historical data in each of the first category and the second category is determined. In an embodiment, the processor 202 may be configured to determine the mean and the variance of the historical data. For example, let A and B represent the first category and the second category, respectively. Let the count of observations (i.e., medical records) in the first category A be $n_A$ and the count of observations in the second category B be $n_B$, where $n_A \gg n_B$. Let the historical observations in the first category A correspond to $x=(x_1, \ldots, x_{n_A})$ and the historical observations in the second category B correspond to $y=(y_1, \ldots, y_{n_B})$. Let d be a dimension of each observation. In an embodiment, each of $x_i$ and $y_i$ follows a Gaussian distribution. The processor 202 may be configured to utilize the following equations to determine the mean and the variance of the historical data for each of the first category and the second category:

$$\hat{\mu}_A = \frac{1}{n_A} \sum_{i=1}^{n_A} x_i \quad (1)$$

$$\hat{\mu}_B = \frac{1}{n_B} \sum_{j=1}^{n_B} y_j \quad (2)$$

$$\hat{\Sigma}_A = \frac{1}{n_A} \sum_{i=1}^{n_A} (x_i - \hat{\mu}_A)(x_i - \hat{\mu}_A)^T \quad (3)$$

$$\hat{\Sigma}_B = \frac{1}{n_B} \sum_{j=1}^{n_B} (y_j - \hat{\mu}_B)(y_j - \hat{\mu}_B)^T \quad (4)$$

where, $\hat{\mu}_A$: Mean of a historical data associated with a first category;

$\hat{\mu}_B$: Mean of the historical data associated with a second category;

$\hat{\Sigma}_A$: Variance of the historical data associated with the first category; and $\hat{\Sigma}_B$: Variance of the historical data associated with the second category.

A person having ordinary skill in the art will understand that the processor 202 may be configured to normalize the measure of the one or more physiological parameters and the one or more lab investigation data (i.e., the historical data) using one or more standard normalization techniques prior to determining the mean and the variance of the historical data for each of the first category and the second category.

At step 308, a first score and a second score are determined. In an embodiment, the processor 202 may be configured to determine the first score and the second score.

In an embodiment, the processor 202 may be configured to determine the first score based on at least the mean and the variance of the historical data categorized in the first category. The processor 202 may further utilize the historical data in the first category to determine the first score. The processor 202 may utilize the following equation to determine the first score ($U_0$).

$$U_0 = \frac{1}{6n_A} \sum_{i=1}^{n_A} \sum_{j=1}^{n_A} \left[ (x_i - \hat{\mu}_A)^T \hat{\Sigma}_A^{-1} (x_j - \hat{\mu}_A) \right]^3 \qquad (5)$$

In an embodiment, the processor 202 may be configured to determine the second score based on at least the mean and the variance of the historical data categorized in the second category. The processor 202 may further utilize the historical data in the second category to determine the second score. The processor 202 may utilize the following equation to determine the second score ($V_0$).

$$V_0 = \frac{1}{6n_B} \sum_{i=1}^{n_B} \sum_{j=1}^{n_B} \left[ (y_i - \hat{\mu}_B)^T \hat{\Sigma}_B^{-1} (y_j - \hat{\mu}_B) \right]^3 \qquad (6)$$

At step 310, the sample data of the first patient is received from the requestor-computing device 102. In an embodiment, the processor 202 may be configured to receive the sample data of the first patient from the requestor-computing device 102 through the transceiver 206 via the input terminal 218. In an embodiment, the sample data may comprise at least the measure of the one or more physiological parameters and the one or more lab investigation data associated with the first patient.

In an embodiment, the processor 202 may be configured to receive the sample data from the requestor-computing device 102. The requestor-computing device 102 may receive the sample data through the DAQ interface 104. The DAQ interface 104 may be connected with the biosensor unit 106 and/or the lab investigation unit 108. The biosensor unit 106, which is connected with the first patient, may be configured to measure the one or more physiological parameters. The lab investigation unit 108 may further be configured to measure the one or more lab investigation data of the first patient. In an embodiment, the DAQ interface 104 may be configured to convert the measured sample data (i.e., the one or more physiological parameters or the one or more lab investigation data) into a digital data type. Thereafter, the DAQ interface 104 may transmit the sample data to the requestor-computing device 102. In another embodiment, the processor 202 may be communicatively coupled to the one or more biosensors such as the sensor 216, which may be configured to measure the one or more physiological parameters of the first patient. Further, the processor 202 may be communicatively coupled (not shown) to the lab investigation unit 108, which may be configured to measure the one or more lab investigation data of the first patient. After receiving the sample data, the processor 202 may be configured to normalize the sample data using the one or more standard normalization techniques known in the art.

At step 312, a first test parameter and a second test parameter are determined. In an embodiment, the processor 202 may be configured to determine the first test parameter and the second test parameter for the sample data (Z). In an embodiment, the processor 202 may determine the first test parameter based on at least the sample data (Z) and the mean and the variance of the historical data associated with the first category. The processor 202 may utilize the following equation to determine the first test parameter ($Z_1$).

$$Z_1 = \frac{1}{6}(Z - \hat{\mu}_A)^T \hat{\Sigma}_A^{-1} (Z - \hat{\mu}_A) \qquad (7)$$

In an embodiment, the processor 202 may determine the second test parameter based on at least the sample data (Z) and the mean and the variance of the historical data associated with the second category. The processor 202 may utilize the following equation to determine the second test parameter ($Z_2$).

$$Z_2 = \frac{1}{6}(Z - \hat{\mu}_B)^T \hat{\Sigma}_B^{-1} (Z - \hat{\mu}_B) \qquad (8)$$

As an illustrative example, consider a bivariate sample data of a first patient, such that a first row is representative of a measure of a physiological parameter such as a heart rate and a second row is representative of a measure of a lab investigation data such as a glucose level. The bivariate sample data is represented as follows:

$$Z = \begin{bmatrix} 0.8 \\ 0.9 \end{bmatrix}$$

Considering a bivariate historical data for each of a first category and a second category, a mean of the first category is assumed as $$\hat{\mu}_A = \begin{bmatrix} 0.5 \\ 0.7 \end{bmatrix}$$

and the mean of the second category is assumed as $$\hat{\mu}_B = \begin{bmatrix} 0.6 \\ 0.8 \end{bmatrix}.$$

Further, it is assumed that the number of observations in the first category is nine and the number of observations in the second category is two. Further, a variance of each of the first category and the second category is assumed as follows:

$$\hat{\Sigma}_A = \begin{bmatrix} 1 & 2 \\ 4 & 3 \end{bmatrix}$$

and $$\hat{\Sigma}_B = \begin{bmatrix} 2 & 3 \\ 6 & 5 \end{bmatrix}$$

In such a case, the processor 202 may determine an inverse of the variance of each of the first category and the second category.

$$\hat{\Sigma}_A^{-1} = \begin{bmatrix} -0.6 & 0.4 \\ 0.8 & -0.2 \end{bmatrix}$$

and $$\hat{\Sigma}_B^{-1} = \begin{bmatrix} -0.625 & 0.375 \\ 0.75 & -0.25 \end{bmatrix}$$

Further, the processor 202 may utilize the equations (such as equations 7 and 8) to determine the first test parameter and the second test parameter.

$$Z_1 = \frac{1}{6}\left(\begin{bmatrix} 0.8 \\ 0.9 \end{bmatrix} - \begin{bmatrix} 0.5 \\ 0.7 \end{bmatrix}\right)^T \begin{bmatrix} -0.6 & 0.4 \\ 0.8 & -0.2 \end{bmatrix} \left(\begin{bmatrix} 0.8 \\ 0.9 \end{bmatrix} - \begin{bmatrix} 0.5 \\ 0.7 \end{bmatrix}\right)$$

$$Z_1 = \frac{1}{6}[0.3 \ 0.2] \begin{bmatrix} -0.6 & 0.4 \\ 0.8 & -0.2 \end{bmatrix} \begin{bmatrix} 0.3 \\ 0.2 \end{bmatrix}$$

$$Z_1 = 0.0016$$

Similarly, $Z_2 = -0.00083$

At step 314, a probability score is determined. The probability score may be utilized to determine whether the sample data is associated with the first category or the second category. In an embodiment, the processor 202 may be configured to determine the probability score based on at least one or more of the first test parameter, the first score, and a test statistic parameter. In an embodiment, the test statistic parameter may correspond to a difference between two independent Chi-squared random variables, which may be determined based on at least the historical data in the first category and the historical data in the second category. In an embodiment, the processor 202 may utilize one or more know techniques to determine the Chi-squared random variables. For example, the test statistic parameter (T) may correspond to $T = \alpha X - \beta Y$. The test statistic parameter (T) represents a difference between two independent Chi-square variables X and Y.

In an embodiment, the processor 202 may utilize the following equations to determine the probability score (p):

$$p = P(T > Z_1 - U_0), \text{ when } Z_1 - U_0 \text{ is positive.} \quad (9)$$

$$p = P(T \leq Z_1 - U_0), \text{ when } Z_1 - U_0 \text{ is negative.} \quad (10)$$

where,
T: test statistic parameter; and
$P(T > Z_1 - U_0)$: CDF of $T > Z_1 - U_0$.

In general, the processor 202 may utilize the following equations to determine the CDF:
Case 1: Large Values of Observed t
For large positive values of t, the CDF may be approximated by:

$$P(T \leq t) \simeq \quad (11)$$

$$\begin{cases} 1 - (2\lambda\beta)^{\frac{-n}{2}} P\left(Z_{y1} \geq \frac{t}{2\alpha}\right), & \text{for large positive } t \text{ and } m \leq 2 \\ 1 - (2\lambda\beta)^{\frac{-n}{2}} \left[\left(\frac{m-2}{2}\right) + \frac{n}{2\lambda\alpha}\right] P\left(Z_{y2} \geq \frac{t}{2\alpha}\right), & \text{for large positive } t \text{ and } m > 2 \end{cases}$$

Similarly, $$P(T \leq -t) \simeq \quad (12)$$

$$\begin{cases} (2\lambda\alpha)^{\frac{-m}{2}} P\left(Z_{y3} \geq \frac{t}{2\beta}\right), & \text{for large positive } t \text{ and } n \leq 2 \\ (2\lambda\alpha)^{\frac{-m}{2}} \left[\left(\frac{n-2}{2}\right) + \frac{m}{2\lambda\beta}\right] P\left(Z_{y4} \geq \frac{t}{2\beta}\right), & \text{for large positive } t \text{ and } n > 2 \end{cases}$$

where,
$T = \alpha X - \beta Y$: Represents a difference between two independent Chi-square variables X and Y;
m, n: Represents degree of freedom of two independent Chi-square variables X and Y, respectively; and
$Z_{y1}, Z_{y2}, Z_{y3}, Z_{y4}$: Represents four Gamma distributed random variables with degree of freedom $$\frac{m}{2}, \frac{m-2}{2}, \frac{n}{2}, \text{ and } \frac{n-2}{2},$$

respectively.
In one embodiment, $$\alpha = \beta = 1, \lambda = \frac{\alpha + \beta}{2\alpha\beta} = 1, \text{ and } m = n = \frac{d(d+1)(d+2)}{6},$$

where d is the dimension of each observation.
Case 2: Small Values of Observed t
For small positive values of t, the CDF may be approximated by:

$$P(T \leq t) \simeq I_{\frac{1}{2\lambda\alpha}}\left(\frac{m}{2}, \frac{n}{2}\right) + A + Be^{-t} \quad (13)$$

where, $$I_{\frac{1}{2\lambda\alpha}}\left(\frac{m}{2}, \frac{n}{2}\right):$$

Incomplete Beta function with the degrees of freedom $$\frac{m}{2} \text{ and } \frac{n}{2}.$$

The values of A and B are conditional on the values of m and n and may further be determined in terms of $$\gamma(m, n, \alpha) = \frac{c(m, n)}{\text{Beta}\left(\frac{m}{2}, \frac{n}{2}\right)} \frac{4\alpha}{m+n-2} \lambda^{-\frac{m+n-2}{2}},$$

where Beta $$\left(\frac{m}{2}, \frac{n}{2}\right)$$

is the Beta distribution with the degrees of freedom $$\frac{m}{2} \text{ and } \frac{n}{2} \text{ and } c(m, n) = \left(2^{\frac{m+n}{2}} \alpha^{\frac{m}{2}} \beta^{\frac{n}{2}}\right)^{-1}.$$

In an embodiment, A=γ(m, n, α) and B=−γ(m, n, α), when 3≤m+n≤4; and $$A = \gamma(m, n, \alpha)\left[1 + \frac{m-2}{m+n-4}2\alpha\lambda^2\right] \text{ and } B = \gamma(m, n, \alpha)\left[1 + \frac{m-2}{m+n-4}4\alpha\lambda^2\right],$$

when m+n≥5.

Further, in an embodiment, the processor 202 may perform similar calculations to determine P(T≤−t).

A person with ordinary skill in the art will understand that the chi-squared random variables may be determined by use of one or more standard techniques/tools/packages known in the art. For example, standard packages in R, Matlab, and Python may be utilized to determine the chi-squared random variables. A standard technique is to first generate n independent and identically distributed (iid) standard normal variables N(0, 1). Then the sum of the square of these variables will be a chi-squared variable with a degree of freedom n.

A person with ordinary skill in the art will understand that Gamma distributed random variables may be determined by use of one or more standard techniques/tools/packages known in the art. For example, standard packages in R, Matlab, and Python may be utilized to determine the Gamma distributed random variables. One standard technique to generate a Gamma variable Z that follows a Gamma(m, 1) distribution is to first generate m iid random variables $U_1$, $U_2$, ..., $U_m$ from a Uniform(0, 1) distribution. Then $X = \Sigma_{\{i=1\}}^m -\log U_i$ will be a Gamma(m, 1) distribution. So, we first generate m iid Uniform(0, 1) distributions and then take the sum of their negative logarithms to generate the Gamma distribution.

Referring back to FIG. 3, at step 316, a check is performed to determine if the probability score is greater than or equal to a predetermined threshold value. In an embodiment, the processor 202 may utilize the comparator 208 to compare the probability score with the predetermined threshold value. If at step 316, it is determined that the probability score is greater than or equal to the predetermined threshold value, then step 324 is performed. If at step 316, it is determined that the probability score is less than the predetermined threshold value, then step 318 is performed.

At step 318, the probability score is updated. In an embodiment, the processor 202 may be configured to update/determine the probability score based on at least the second test parameter, the second score, and the test statistic parameter. For example, the processor 202 may utilize the following equations to determine the probability score (p):

$$p = P(T > Z_2 - V_0), \text{ when } Z_2 - V_0 \text{ is positive.} \quad (14)$$

$$p = P(T \leq Z_2 - V_0), \text{ when } Z_2 - V_0 \text{ is negative.} \quad (15)$$

Further, in an embodiment, the processor 202 may utilize one or more of equations (e.g., equations 11-13) to determine the updated probability score.

At step 320, a check is performed to determine if the updated probability score is greater than or equal to the predetermined threshold value. In an embodiment, the processor 202 may utilize the comparator 208 to compare the probability score with the predetermined threshold value. If at step 320, it is determined that the probability score is greater than or equal to the predetermined threshold value, then step 326 is performed. If at step 320, it is determined that the probability score is less than the predetermined threshold value, then step 322 is performed.

At step 322, a check is performed to determine if a mean squared deviation (MSD) of the sample data (Z) from the historical data (x) in the first category is less than the mean squared deviation (MSD) of the sample data (Z) from the historical data (y) in the second category. If at step 326, it is determined that the MSD of the sample data (Z) from the historical data (x) in the first category is less than the MSD of the sample data (Z) from the historical data (y) in the second category, then step 324 is performed. If at step 326, it is determined that the MSD of the sample data (Z) from the historical data (x) in the first category is greater than or equal to the MSD of the sample data (Z) from the historical data (y) in the second category, then step 326 is performed.

At step 324, the sample data of the first patient is categorized into the first category. In an embodiment, the processor 202 may be configured to categorize the sample data of the first patient in the first category. For example, a predetermined threshold value is equal to 0.025 and a probability score of a sample data has been determined as 0.036. The comparator 208 determines that the probability score (p=0.036) is greater than the predetermined threshold value (0.025). In such a scenario, the processor 202 may include the sample data into the first category. In another illustrative example, the processor 202 may categorize the sample data of the first patient in the first category if the processor 202 determines that $$\frac{1}{n_A}\sum_{i=1}^{n_A}(Z-x_i)^2 < \frac{1}{n_B}\sum_{j=1}^{n_B}(Z-y_j)^2.$$

At step 326, the sample data of the first patient is categorized into the second category. In an embodiment, the processor 202 may be configured to categorize the sample data of the first patient in the second category. For example, a predetermined threshold value is equal to 0.025 and a probability score for a sample data has been determined as 0.029. The comparator 208 determines that the probability score (p=0.029) is greater than the predetermined threshold value (0.025). In such a scenario, the processor 202 may include the sample data into the second category. In another illustrative example, the processor 202 may categorize the sample data of the first patient in the second category if the processor 202 determines that $$\frac{1}{n_A}\sum_{i=1}^{n_A}(Z-x_i)^2 \geq \frac{1}{n_B}\sum_{j=1}^{n_B}(Z-y_j)^2.$$

At step 328, the mortality of the first patient is predicted based on at least the determined category of the sample data of the first patient. In an embodiment, the processor 202 may be configured to predict the mortality of the first patient based on at least the determined category of the sample data of the first patient. For example, a sample data of a first patient is categorized under the first category. In such a case, a likelihood of survival of the first patient is more than the likelihood of death. In case the sample data is categorized under the second category, the likelihood of survival of the first patient is less than the likelihood of death. Further, in an embodiment, the processor 202 may be configured to display the predicted mortality status of the first patient through a user-interface on the requestor-computing device 102.

A person having ordinary skill in the art will understand that the scope of the disclosure should not be limited to predicting the mortality status of the first patient. In an embodiment, the processor 202 may analyse other medical data sets in a similar manner to predict other health conditions. For example, the other health conditions may correspond to at least one of a disease risk, a disease symptom, an onset of a disease, a recovery from a disease, or an effect of medications for a disease.

Further, in an embodiment, a set of classifiers may be trained based on the processes as discussed above in steps 302-328. In an embodiment, the processor 202 may be configured to train the set of classifiers. In an embodiment, the processor 202 may train the set of classifiers based on at least one or more of the historical data, the mean, the variance, the probability score, the first score, the second score, the first test parameter, the second test parameter, the test statistic parameter, and the one or more rules as discussed in step 314. Further, in an embodiment, the processor 202 may train the set of classifiers using one or more machine learning techniques known in the art. Examples of one or more classifiers may include, but are not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier.

A person having ordinary skills in the art will appreciate that the scope of the disclosure is not limited to the training of the set of classifiers, as discussed above. The set of classifiers may be trained using any machine learning or artificial intelligence technique known in the art without departing from the spirit of the disclosure.

Figure 4:
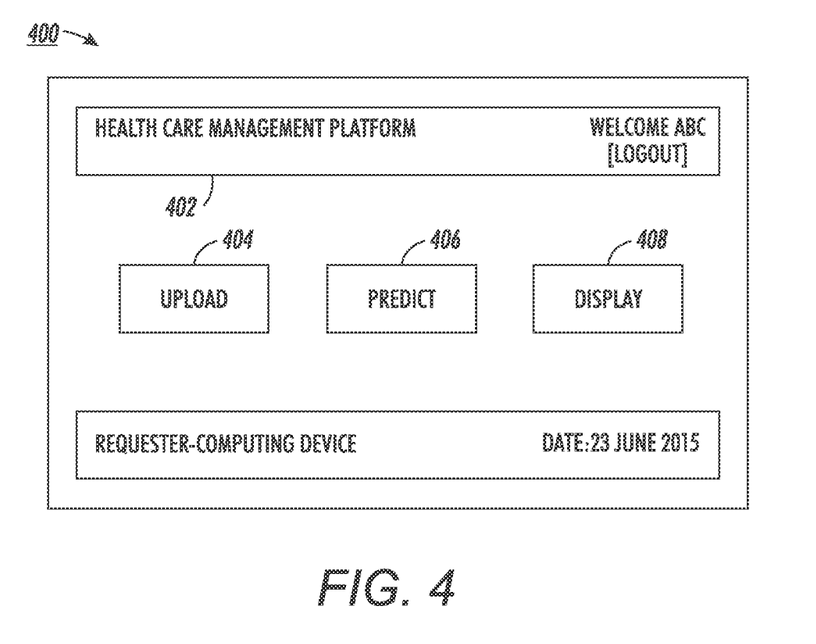
FIG. 4 is a block diagram illustrating an example graphical user-interface that may be utilized by a requestor to initiate mortality prediction of a first patient, in accordance with at least one embodiment.

FIG. 4 is a block diagram illustrating an example graphical user-interface (GUI) 400 that may be utilized by the requestor to initiate the prediction of the mortality of the first patient, in accordance with at least one embodiment. The GUI 400 may be displayed on the display screen of the requestor-computing device 102. The requestor may log into a platform such as a healthcare management platform 402 using his/her user id and password. The processor 202 may present the GUI 400 on the requestor-computing device 102, when the requestor may have logged in. The requestor may click on a tab such as upload tab 404 to upload the sample data of the first patient. Further, the user may utilize the upload tab 404 to upload the historical data of the one or more second patients. Further, the user may utilize the upload tab 404 to input one or more predetermined parameters such as the predetermined threshold value. The requestor may click on a tab such as predict tab 406 to initiate the process of predicting the mortality of the first patient. After prediction has been completed, the processor 202 may generate a pop-up message displaying one or more notification messages such as "categorization of sample data completed". Thereafter, the requestor may click on a tab such as a display tab 408 to view the categorization of the sample data and/or the mortality status of the first patient.

The disclosed embodiments encompass numerous advantages. The method discloses a classification method for classifying the imbalanced dataset. The disclosed method exploits the imbalance in the dataset to achieve the transformation such that the transformed features are well separated. The method discloses transforming the Gaussian random variables into the Chi-squared random variables where the degree of freedom depends on the mean, the variance, and the size of the category in the training data. Further, the disclosed method may be utilized in the healthcare industry to predict the mortality of the patients. Based on at least the mortality prediction, precautionary and necessary steps may be taken to reduce the risk of deaths in the patients. The disclosed classification method may further be utilized in the field of finance industry to identify defaulters or in a call centre industry where an automatic routing of calls may be essential to identify a high priority call which are fewer in number.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++" and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of methods and systems for predicting mortality of a patient have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method of operating a patient viability system, said method comprising:

extracting, by one or more processors, historical patient data associated with a plurality of past patients previously under medical observation, wherein the historical patient data comprises measurements of a physiological parameter associated with each of the plurality of past patients;

categorizing, by the one or more processors, the historical patient data into a first category and a second category, wherein the first category comprises a first subset of the historical patient data corresponding to patients who survived under medical observation, the second category comprises a second subset of the historical patient data corresponding to patients who died under medical observation, and a number of past patients in the first subset is substantially greater than in the second subset;

receiving, by the one or more processors, a sample data of a patient currently under medical observation, the sample data comprising a measurement of the physiological parameter associated with the patient;

determining, by the one or more processors, a first test parameter and a second test parameter based on at least one of the sample data and the historical patient data corresponding to at least one of the first category and the second category;

determining, by the one or more processors, a probability score based on a cumulative distribution of at least one of the first test parameter and the second test parameter;

categorizing, by the one or more processors, the sample data of the patient, in one of the first category and the second category, based on a comparison between the probability score and a predetermined threshold value, and based on a mean squared transformation of the sample data using the historical patient data corresponding to the first and second categories; and generating, by the one or more processors, a viability report for the patient based on at least the categorization of the sample data of the patient, wherein the viability report indicates a likelihood of the patient dying while under the medical observation.

2. The method of claim 1, wherein the historical patient data further comprise lab investigation data comprising one or more of a sodium level, a potassium level, a glucose level, and a cholesterol level.

3. The method of claim 1 further comprising measuring, by one or more sensors, the physiological parameter of the patient to obtain the measurement, wherein the physiological parameter comprises one or more of blood pressure, heart rate, respiratory rate, body temperature, and oxygen saturation.

4. The method of claim 1, wherein the sample data further comprises lab investigation data.

5. The method of claim 1 further comprising determining, by the one or more processors, a mean, for each of the first category and the second category, based on the historical patient data associated with each of the first category and the second category.

6. The method of claim 5 further comprising determining, by the one or more processors, a variance, for each of the first category and the second category, based on the mean and the historical patient data associated with each of the first category and the second category.

7. The method of claim 6 further comprising determining, by the one or more processors, a first score and a second score based on at least one of the mean, the variance, and the historical patient data associated with at least one of the first category and the second category.

8. The method of claim 7, wherein the first test parameter and the second test parameter are further determined based on at least one of the mean and the variance corresponding to each of the first category and the second category.

9. The method of claim 8, wherein the probability score is determined based on at least one of the first test parameter, the second test parameter, the first score, the second score, and a test statistic parameter, wherein the test statistic parameter corresponds to a difference between two independent Chi-squared random variables.

10. The method of claim 9, wherein the probability score is compared, by a comparator coupled to the one or more processors, with the predetermined threshold value corresponding to at least one of the first test parameter and the second test parameter.

11. A patient viability system comprising:
one or more processors configured to:
extract historical patient data associated with a plurality of past patients previously under medical observation, wherein the historical patient data comprises measurements of a physiological parameter associated with each of the plurality of past patients;
categorize the historical patient data into a first category and a second category, wherein the first category comprises a first subset of the historical patient data corresponding to patients who survived under medical observation, the second category comprises a second subset of the historical patient data corresponding to patients who died under medical observation, and a number of past patients in the first subset is substantially greater than in the second subset;
receive a sample data of a patient currently under medical observation, the sample data comprising a measurement of the physiological parameter associated with the patient;
determine a first test parameter and a second test parameter based on at least one of said sample data of the patient and the historical patient data corresponding to at least one of the first category and the second category;
determine a probability score based on a cumulative distribution of at least one of the first test parameter and the second test parameter;
categorize the sample data of the patient, in one of the first category and the second category, based on a comparison between the probability score and a predetermined threshold value, and based on a mean squared transformation of the sample data using the historical patient data corresponding to the first and second categories; and
generate a viability report for the patient based on at least the categorization of the sample data of the patient, wherein the viability report indicates a likelihood of the patient dying while under the medical observation.

12. The system of claim 11 further comprising one or more sensors configured to measure the physiological parameter of the patient to obtain the measurement, wherein the physiological parameter comprises one or more of blood pressure, heart rate, respiratory rate, body temperature, and oxygen saturation.

13. The system of claim 11, wherein the one or more processors are further configured to determine a mean, for each of the first category and the second category, based on the historical patient data associated with each of the first category and the second category.

14. The system of claim 13, wherein the one or more processors are further configured to determine a variance, for each of the first category and the second category, based on the mean and the historical patient data associated with each of the first category and the second category.

15. The system of claim 14, wherein the one or more processors are further configured to determine a first score and a second score based on at least one of the mean, the variance, and the historical patient data associated with at least one of the first category and the second category.

16. The system of claim 15, wherein the one or more processors are further configured to determine the first test parameter and the second test parameter based on at least one of the sample data of the patient, the mean and the variance corresponding to each of the first category and the second category.

17. The system of claim 16, wherein the one or more processors are further configured to determine the probability score based on at least one of the first test parameter, the second test parameter, the first score, the second score, and a test statistic parameter, wherein the test statistic parameter corresponds to a difference between two independent Chi-squared random variables.

18. The system of claim 17 further comprising a comparator coupled to the one or more processors, and configured to compare the probability score with the predetermined threshold value corresponding to at least one of the first test parameter and the second test parameter.

19. A computer program product for use with a computer, the computer program product comprising a non-transitory computer readable medium, wherein the non-transitory computer readable medium stores a computer program code for operating a patient viability system, wherein the computer program code is executable by one or more processors to:
extract historical patient data associated with a plurality of past patients previously under medical observation, wherein the historical patient data comprises a measure of a physiological parameter associated with each of the plurality of past patients;
categorize the historical patient data into a first category and a second category, wherein the first category comprises a first subset of the historical patient data corresponding to patients who survived under medical observation, the second category comprises a second subset of the historical patient data corresponding to patients who died under medical observation, and a number of past patients in the first subset is substantially greater than in the second subset;
receive a sample data of a patient currently under medical observation, the sample data comprising a measurement of the physiological parameter associated with the patient;
determine a first test parameter and a second test parameter based on at least one of said sample data of the patient and the historical patient data corresponding to at least one of the first category and the second category;
determine a probability score based on a cumulative distribution of at least one of the first test parameter and the second test parameter;
categorize the sample data of the patient, in one of the first category and the second category, based on a comparison between the probability score and a predetermined threshold value, and based on a mean squared transformation of the sample data using the historical patient data corresponding to the first and second categories; and
generate a viability report for the patient based on at least the categorization of the sample data of the patient, wherein the viability report indicates a likelihood of the patient dying while under the medical observation.

20. The method of claim 1, wherein the number of past patients in the first subset is at least ten-fold greater than in the second subset.

* * * * *